United States Patent [19]

Gors et al.

[11] Patent Number: 4,814,508

[45] Date of Patent: Mar. 21, 1989

[54] FRIEDEL-CRAFTS PREPARATION OF AROMATIC KETONES

[75] Inventors: Heinrich C. Gors, Mountain View; Patrick J. Horner, Menlo Park; Viktors Jansons, Los Gatos, all of Calif.

[73] Assignee: Raychem Corporation, Menlo Park, Calif.

[21] Appl. No.: 175,646

[22] Filed: Mar. 21, 1988

Related U.S. Application Data

[63] Continuation of Ser. No. 874,269, Jun. 13, 1986, abandoned, which is a continuation-in-part of Ser. No. 789,546, Oct. 22, 1985, abandoned, and Ser. No. 659,598, Oct. 11, 1984, abandoned.

[51] Int. Cl.$^4$ .................. C07C 107/06; C07C 49/813; C07C 49/83; C07C 49/84
[52] U.S. Cl. .................. 568/309; 534/588; 534/593; 568/322; 568/323; 568/325; 568/332
[58] Field of Search .............. 534/588, 593; 568/309, 568/322, 323, 325, 332

[56] References Cited

U.S. PATENT DOCUMENTS

| | | | |
|---|---|---|---|
| 1,874,580 | 8/1932 | Nawiasky | 568/333 X |
| 2,773,903 | 12/1956 | Hardy et al. | 568/333 |
| 2,853,522 | 9/1958 | Dayan et al. | 568/333 |
| 2,853,523 | 9/1958 | von Glahn et al. | 568/333 |
| 2,861,104 | 11/1958 | von Glahn et al. | 568/333 |
| 2,861,105 | 11/1958 | Stanley et al. | 568/333 |
| 3,282,989 | 11/1966 | Renckoff et al. | 568/333 X |

FOREIGN PATENT DOCUMENTS

| | | | |
|---|---|---|---|
| 0024286 | 3/1981 | European Pat. Off. | 568/332 |
| 0069598 | 1/1983 | European Pat. Off. | 568/332 |
| 878647 | 9/1952 | Fed. Rep. of Germany | 568/332 |
| 913891 | 11/1953 | Fed. Rep. of Germany | 568/332 |
| 2014514 | 10/1970 | Fed. Rep. of Germany | 568/332 |
| 384813 | 5/1973 | U.S.S.R. | 568/332 |
| 384807 | 5/1973 | U.S.S.R. | 568/332 |
| 1088339 | 10/1967 | United Kingdom | 540/122 |
| 1420506 | 1/1976 | United Kingdom | 568/332 |
| 2103604A | 2/1983 | United Kingdom | 568/333 |

OTHER PUBLICATIONS

Freitag, Chem. Abs. 95:43910a.
Windholz, Chem. Abs. 73:120343t.
Braun, III, Chem. Abs. 50:4229i.
Braun, IV, Chem. Abs. 52:14691f.
Moshehisnkaya, Chem. Abs. 79:104903u.
Olah, "Friedel-Crafts and Related Reactions", vol. I, Interscience Publishers, Inc., N.Y., pp. 91 to 109, 120, 122, 123 and 212 to 304 (1963).

*Primary Examiner*—Floyd D. Higel
*Attorney, Agent, or Firm*—Yuan Chao; Edith A. Rice; Herbert G. Burkard

[57] ABSTRACT

Aromatic carbonyl compounds, in particular arylene ether ketones, are prepared by reacting an appropriate reagent system in the presence of free Lewis acid and a complex between a Lewis acid, for example, aluminum trichloride, and a Lewis base, for example, N,N-dimethylformamide, and, optionally, a diluent, such as methylene chloride. The process is particularly advantageous for the preparation of substantially or all para-linked arylene ether ketones as the presence of the Lewis acid/Lewis base complex markedly reduces alkylation and ensures the substantial absence of ortho substitution.

7 Claims, No Drawings

FRIEDEL-CRAFTS PREPARATION OF AROMATIC KETONES

This applicaiton is a continuation of application Ser. No. 874,269, filed Jun. 13, 1986, now abandoned, which is a continuation-in-part of application Ser. No. 789,546, filed Oct. 22, 1985, now abandoned, and of application Ser. No 659,598, filed Oct. 11, 1984, now abandoned, the disclosures of which are incorporated herein by reference.

BACKGROUND OF THE INVENTION

This invention relates to the preparation of aryl carbonyl compounds, and in particular to para substituted aryl carbonyl compounds.

Aryl carbonyl compounds are useful in the preparation of poly(arylene ether ketones). In the preparation of these polymers it is essential that the monomers used be in a highly pure state to prevent undesirable side reactions. Furthermore, the polymers obtained should be stable enough to survive extrusion without undue deleterious effects on their physical properties. The substitution pattern of the monomers used can control the properties of the polymers synthesised, and it is generally recognized that the highest melting points and glass-rubber transition temperatures are obtained with all para linked polymers. Mixtures of substitution isomers are used when polymers of reduced crystallinity or lowered Tg are required, but the all para substituted polymers are most preferred. When mixtures of monomers are used, known ratios of the different isomers are needed, necessitating the use of pure starting materials. The present invention relates to a process for the preparation of aryl carbonyl compounds that improves outstandingly the degree of purity of the product and/or the degree of para substitution.

Aryl carbonyl compounds are also useful as chemicals and chemical intermediates, for example, in the pharmaceutical and agricultural chemicals, dyestuffs and general chemical additives area. Here too it is frequently found that the all para substituted carbonyl compounds are the most useful. Avoidance of concurrent formation of other isomeric byproducts in the synthesis of such compounds is always beneficial economically and in some instances is essential because some isomeric compounds which are difficult to remove have been found to be toxic or even carcinogenic.

SUMMARY OF THE INVENTION

In accordance with the process of this invention, the Friedel-Crafts condensation of appropriate reactants is controlled to suppress side reactions including alkylation and/or ortho substitution by conducting the reaction under select reaction conditions and proportions of reactants not taught or suggested by the prior art or by the addition of a controlling agent, such as a Lewis base, to the reaction medium or both.

One aspect of this invention comprises a method of producing an aryl carbonyl compound which comprises reacting phosgene or an organic carboxylic acid, acid halide, alkyl ester or anhydride together with an aromatic comonomer containing at least one activated hydrogen atom in the presence of a Lewis acid, optionally a controlling agent, and a nonprotic diluent, the various components being present in such proportions and the reaction being conducted underssuch conditions that a para substituted carbonyl compound substantially free of by-products resulting from alkylation and/or ortho substitution is obtained.

Another aspect of this invention provides a process for the preparation of an aromatic carbonyl compound having the formula (R)$_s$ArDCOY, (R)$_s$ArDCOBD(R')$_t$, (R)$_s$ArDCOBD-COArD(R)$_s$,
(R)$_s$ArDCODAr(R)$_s$, or (R')$_t$DBCOArDCOBD(R')$_t$ wherein each s and t is independently 1, 2 or 3 and each R, Ar, B, D and R' are independently as defined below, which process comprises reacting a first reactant, consisting of a substituted or unsubstituted aromatic compound containing at least one activated hydrogen atom of the formula

wherein Ar is a homo or hetero-aromatic mono-, di- or tricyclic moiety or a fused homo-aromatic condensed system containing less than 20 aromatic carbon atoms, or a hetero-aromatic system containing less than 8 nitrogen atoms, each R is as defined below and D is

wherein n, m, and p are each independently 0, 1, 2 or 3, provided that n+m+p is less than 4, and Z is —CO—, —SO$_2$—,

—O(CF2)qO— or V, provided that when n+m+p>0, any Ar group which contains an activated hydrogen atom is also linked to a V group, where V is a divalent radical of the formula

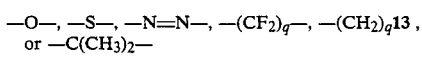

wherein q is 1 to 20;
with a second reactant, consisting of phosgene, or a monofunctional acyl compound of the general formula

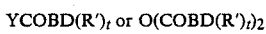

or a di-functional acyl compound of the general formula

wherein each B is independently a divalent substituted or unsubstituted aliphatic or cycloaliphatic group or Ar, and R and R' which may be the same or different are, a H, Br, Cl or F atom or a hydroxy, alkoxy, alkyl, aralkyl, unsubstituted or mono- or disubstituted amino, nitro, ester, acid, amide or imide group, and each Y represents a Br, Cl or F atom or a hydroxy or alkoxy group, subject to the proviso that any aromatic ring which contains an activated hydrogen atom also contains less than 2 alkoxy groups and to the further proviso that the aromatic carbonyl compound contains less than 2 identical directly linked sequences containing at least one —SO$_2$—or —CO—
in a reaction medium comprising:
(A) a Lewis base in an amount from 0 to 4 equivalents per equivalent of acid, ester or acid halide group in the reactants;

(B) a Lewis acid in an amount of about one equivalent per equivalent of carbonyl, or other basic species in the reactants plus one equivalent per equivalent of Lewis base plus an amount effective to act as a catalyst for the reaction;
and (C) a non-protic diluent in an amount from about 20 to about 93% by weight, based on the weight of the total reaction mixture;

with the proviso that in the substantial absence of Lewis base the Lewis acid is present in an amount in excess of that specified in (A) above, by at least about 0.5 but less than about 4 equivalents per equivalent of acid, ester or acid halide groups in the reactants.

Pendant substituents which can be present on B or Ar groups include, for example, lower alkyl, cyano, halogen, nitro, benzoyl or any other atom or group which will not interfere with the reaction by virtue of either its chemical nature or its location in the reactant from which the B group is derived.

DETAILED DESCRIPTION OF THE INVENTION

The term "activated hydrogen atom" refers to a hydrogen atom displaceable under the electrophilic (Friedel-Crafts) reaction conditions employed in the reaction.

Aromatic compounds suitable for acylation according to the process of the instant invention exhibit carbon-13 nuclear magnetic resonance (C-13 NMR) chemical shifts at the ring site where acylation is desired at least 2.1, preferably at least 2.4 and most preferably at least 2.8 parts per million (ppm) less than that exhibited by benzene. For a listing of C-13 NMR chemical shifts of monosubstituted benzenes see M. Mishima et al (Memoirs of the Faculty of Science, Kyushu Un., Ser. C, Vol. 11 No. 1, 1978) hereby incorporated by reference. Table 2 of this reference lists C-13 NMR chemical shifts of a variety of mono-substituted benzenes measured in solution in carbon tetrachloride. Benzene in this solvent is stated to have a chemical shift of 128.04 ppm. The aromatic compounds useful in the instant invention may, but preferably do not, form additional complexes with Lewis acid under the reaction conditions. Those skilled in the art will readily recognize that when an addition complex is formed, it should not substantially deactivate the molecule to acylation. Thus such complexes, for example, should still exhibit C-13 NMR chemical shifts which are at least 2.1 ppm less than that of benzene or should sufficient uncomplexed aromatic compound is present to enable the reaction to proceed at the desired rate.

Illustrative aromatic compounds of the general formulas (R)$_s$ Ar DH are: benzene, toluene, ethyl benzene, fluorobenzne, anisole, ethoxy benzene, 3-chloroanisole, napthalene, anthracene and

-continued

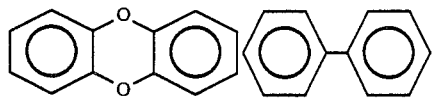

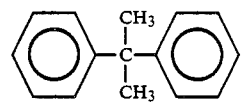

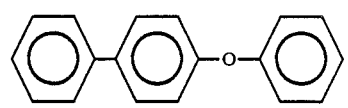

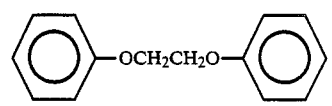

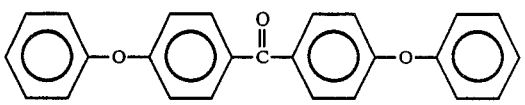

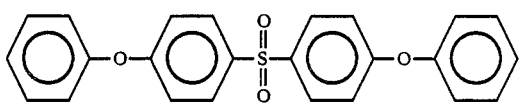

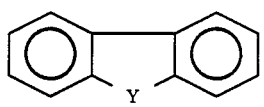

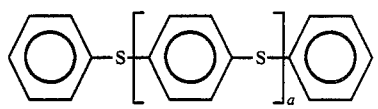

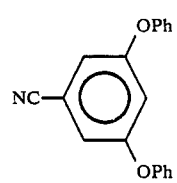

wherein each a is independently 0, 1 or 2 and V is as defined above.

Illustrative mono or di-acyl compounds of the general formula

YCOBD(R')$_t$, O(COBD(R')$_t$)$_2$ or YCOBDCOY are: acetic anhydride, acetyl chloride, adipoyl dichloride, benzoyl chloride, 4-fluorobenzoyl chloride, 4- chlorobenzoyl chloride, 3nitrobenzoyl chloride, phthaloyl chloride, phthalic anhydride, naphthoyl chloride, benzenesulfonyl chloride, p-toluenesulfonyl chloride, tetrabromophthaloyl chloride, an compounds of the following formulas

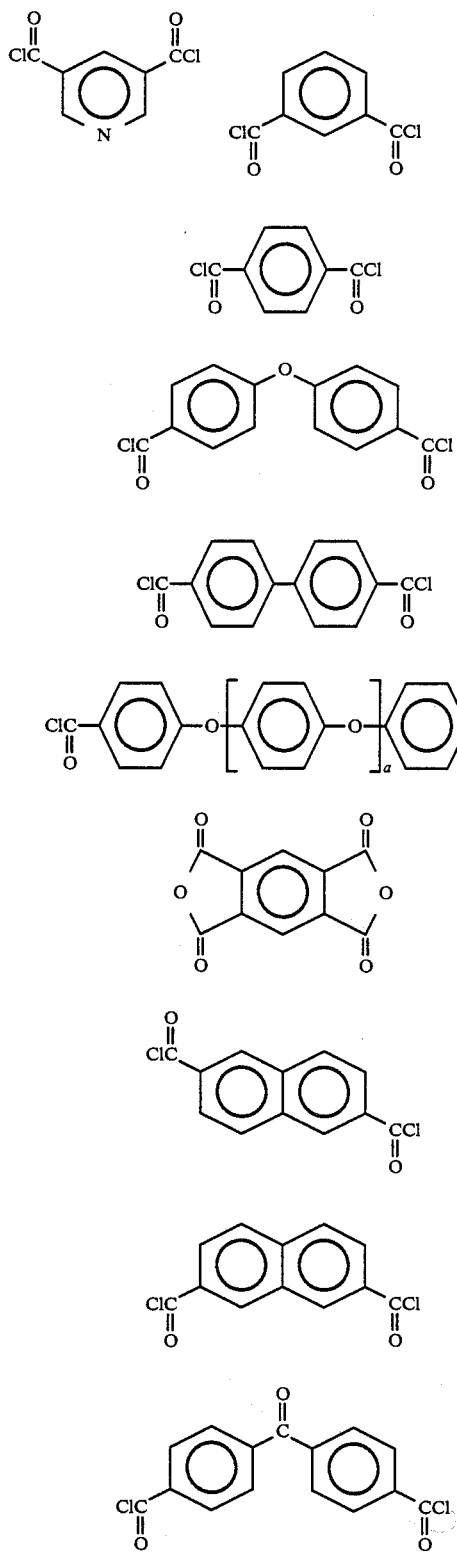

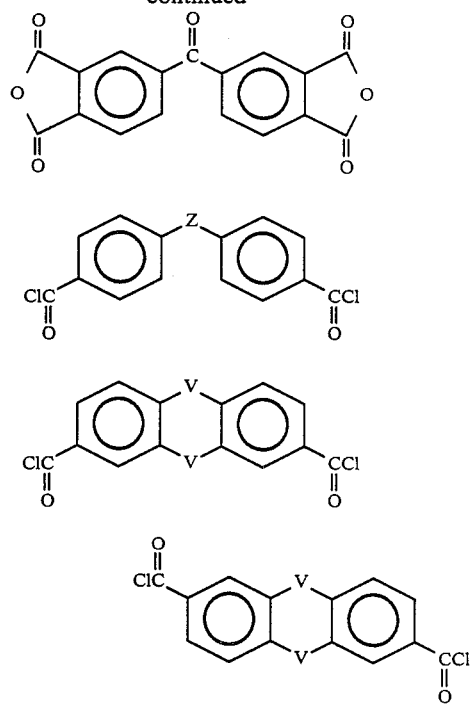

wherein each V is independently as defined above and Z and a are as defined above.

Preferred acylating agents are phosgene, sulfuryl chloride and acyl compounds such as 4-fluorobenzoic acid or acid halide, iso- or tere-phthalic acid or acid halide, naphthalene 2,6-dicarboxylic acid or acid halide, diphenyl ether 4,4'-dicarboxylic acid or acid chloride and benzophenone 4,4'-dicarboxylic acid or acid chloride.

Preferred combinations of substituted aromatic compounds and acyl compounds are fluorobenzene or diphenyl ether with 4-fluorobenzoyl chloride, ethyl 4-fluorobenzoate, acetYl chloride, acetic anhydride, iso- or tere-phthaloyl chloride, 4-hydroxybenzoyl chloride and 4-(4-hydroxy phenoxy)-benzoyl chloride.

In carrying out the process of this invention, equivalent amounts of the substituted aromatic compound and the aromatic acyl compound are preferably employed, although it may be advantageous in certain circumstances to use up to about a molar excess of one reactant.

The reagent system is reacted in the presence of a reaction medium comprising:
(A) a Lewis base in an amount from 0 to 4 equivalents per equivalent of acid, ester or acid halide group in the reactants;
(B) a Lewis acid in an amount of about one equivalent per equivalent of carbonyl or other basic species in the reactants plus one equivalent per equivalent of Lewis base plus an amount effective to act as a catalyst for the reaction; and
(C) a non-protic diluent in an amount from about 20 to about 93% by weight, based on the weight of the total reaction mixture;
with the additional proviso that in the substantial absence of Lewis base the Lewis acid is present in an amount in excess of that specified in (A) above, by at least about 0.5 but less than about 4 equivalents per equivalent of acid, ester or acid halide groups in the reactants.

The term "Lewis acid" is used herein to refer to a substance which can accept an unshared electron pair from another molecule. Lewis acids which can be used in the practice of this invention include, for example, aluminum trichloride, aluminum tribromide, antimony pentachloride, antimony pentafluoride, indium trichloride, gallium trichloride, boron trichloride, boron trifluoride, zinc chloride, ferric chloride, stannic chloride, titanium tetrachloride, and molybdenum pentachloride. The use of substantially anhydrous aluminum trichloride as the Lewis acid is preferred. ferred.

The amount of Lewis acid used in the practice of this invention varies dependigg on the particular starting materials and reaction medium selected. In all instances where the Lewis acid forms a complex with carbonyl groups or other organic species in the reactants forming a complex with Lewis acid (hereinafter called "other basic species") irreversibly under the reaction conditions, at least about one equivalent of Lewis acid per equivalent of carbonyl groups or other basic species present in the starting materials is used plus an amount effective to act as a catalyst for the acylation. Generally the catalytic amount added is from about 0.05 to about 0.3 equivalents of Lewis acid per equivalent of acid, ester or acid halide in the reaction mixture. As is well known to those skilled in the art, acids, esters and many acid anhydrides react with an excess of Lewis acids such as aluminum trichloride to yield the corresponding acid halide which then serves as the actual acylating agent. As indicated above, the FriedelCrafts acylation reaction is controlled by the addition of a controlling agent or by varying the reaction conditions, including varying the amount of Lewis acid to achieve the desired compound substantially free of isomric by-products.

In a preferred embodiment of the invention, the controlling agent suppresses undesirable side reactions, whether by acylation or by alkylation.

Preferred controlling agents for the acylation reaction are Lewis bases. The term "Lewis base" is used herein to refer to a substance capable of donating an unshared electron pair to a Lewis acid. Thus, the Lewis base forms a complex with the Lewis acid used in the reaction medium. It has been found that Lewis bases which form a 1:1 complex having a heat of association at least about that of diphenyl ether with the Lewis acid are preferred. For example, where aluminum trichloride is the Lewis acid the Lewis base used should form a 1:1 complex having a heat of association of at least about 15 kcal/mole, preferably at least about 30 kcal/mole. While the heats of association are for a 1:1 Lewis acid/Lewis base complex consisting solely of these two components, the actual complex formed in the reaction medium need not be a 1:1 complex. A discussion on heats of association for Lewis acid/Lewis base complexes is found in J. Chem. Soc. (A), 1971, pages 3132–3135 (D.E.H. Jones et al). The Lewis base used should not be an acylating, alkylating or arylating agent nor should it be acylatable under the reaction conditions.

Mixtures of two or more Lewis bases can be used if desired. The Lewis base used as a controlling agent in the practice of this invention is an additional component added to the reaction medium. This does not include basic species formed in situ during the acylation. When a Lewis base is used as a controlling agent, an additional amount of Lewis acid generally about one equivalent per equivalent of Lewis base is used. When aluminum chloride is used as the Lewis acid one equivalent is considered to be $AlCl_3$.

Typical Lewis bases which can be employed include, for example, amides, amines, esters, ethers, ketones, nitriles, nitro compounds, phosphines, phosphine oxides, phosphoramides, sulfides, sulfones, sulfonamides, sulfoxides and halide salts.

Examples of specific organic Lewis bases that can be used in the practice of this invention are acetone, benzophenone, cyclohexanone, methyl acetate, ethylene carbonate, N-methylformamide, acetamide, N,N-dimethylacetamide, N-methylpyrrolidone, urea, tetramethylurea, N-acetylmorpholine, dimethyl sulfoxide, N,N-dimethylformamide, diphenyl sulfone, dimethyl sulfone, N,N-dimethylmethanesulfonamide, phosphoryl chloride, phenylphosphonyl chloride, pyridine-N-oxide, triphenylphosphine oxide, trioctylphosphine oxide, nitoopropane, nitrobenzene, benzonitrile, n-butyronitrile, methyl ether, tetrahydrofuran, dimethyl sulfide, trimethylamine, N,N,N',N'-tetramethylethylenediamine, N,N-dimethyldodecylamine, imidazole, pyridine, quinoline, isoquinoline, benzimidazole, 2,2'-bipyridine, o-phenanthroline, 4-dimethylaminopyridine, and the like. In addition to covalent organic compounds, suitable Lewis bases include inorganic salts which can form complexes with Lewis acids, for example, chlorides, such as trimethylammonium chloride, tetramethylammonium chloride, sodium chloride or lithium chloride, perchlorates, trifluoromethanesulfonates and the like.

Preferred Lewis bases for the practice of this invention are N-methylformamide, N,N-dimethylformamide, N,N-dimethylacetamide, 1-methyl-2-pyrrolidone, tetramethylene sulfone (also known as Sulfolane), n-butyronitrile, dimethyl sulfide, imidazole, acetone, benzophenone, trimethylamine, trimethylamine hydrochloride, tetramethylammonium chloride, pyridine-N-oxide, 1-ethylpyridinium chloride, lithium chloride, lithium bromide, sodium chloride, sodium bromide, potassium chloride, potassium bromide and mixtures thereof.

The amount of Lewis base present should be from 0 to about 4 equivalents per equivalent of acid halide groups present in the reagent system. Amounts greater than 4 equivalents could be employed, if desired. However, no additional controlling effect is usually achieved by adding larger amounts. Thus, it is preferred to use no more than about 4 equivalents and generally about 2 equivalents. When a Lewis base is added to control the reaction at least about 0.1, preferably at least about 0.2 and most preferably at least about 0.5 equivalents of Lewis base per equivalent of acid halide groups present should be used. The particular amount of Lewis base added depends to a certain extent on the nature of the monomers present.

The temperature at which the reaction is conducted can be from about $-50°$ C. to about $+150°$ C. It is preferred to start the reaction at lower temperatures, for example at about $-50°$ to about $-10°$ C. particularly if the reaction mixture contains highly reactive reagents. After acylation has commenced, the temperature can be raised up to about 150° C. or even higher if desired, for example, to increase the rate of reaction. It is generally preferred to carry out the reaction at temperatures in the range of between about $-30°$ C. and $+25°$ C. (room temperature).

A non-protic diluent can also be employed, if desired. Advantageously, the diluent should dissolve the Lewis acid/Lewis base complex and the Lewis acid/acyl compound complex. It should also be relatively inert toward Friedel-Crafts reactions. Preferred diluents include, for example, methylene chloride, carbon disulfide, o-dichlorobenzene, 1,2,4-trichlorobenzene, o-difluorobenzene, 1,2-dichloroethane, 1,1,2-trichloroethene, 1,1,2,2-tetrachloroethane, tetrachloroethene and mixtures thereof. In certain cases it may be advantageous to use an excess of the aromatic reactant, which also serves as a solvent for the reaction.

If a diluent such as methylene chloride or dichloroethane is used, although we do not wish to be bound to any particular explanation it is believed that the Lewis acid/Lewis base complex reduces the tendency of the diluent to act as an alkylating agent by competing with the diluent for available Lewis acid and thereby suppressing alkylation of reactant and/or product. Alkylation of the aromatic component in the para or ortho position introduces undesirable impurities which often are difficult to remove by conventional purification methods.

The diluent is preferably used in an amount from 20 to about 93% by weight, based on the weight of the total reaction mixture whether or not a Lewis base is used. It has been found that the reagent to diluent molar ratio can contribute to control of the reaction to yield the desired product. Typically the diluent is used in an amount of at least about 20%, preferably at least about 30% by weight based on the weight of the reaction mixture. Typically the diluent is also used in an amount of less than 93%, preferably less than 80%, most preferably less than 60%.

Use of an alkylating or acylating diluent can lead to undesired side reactions as mentioned above. When such solvents are employed, control of the reaction by techniques taught in this specification suppresses such alkylation or arylation. The result is an aryl carbonyl or sulfonyl compound of outstanding purity and/or degree of para substitution.

The reaction can also be controlled by use of the appropriate reaction conditions without the addition of a Lewis base. The term substantial absence of Lewis base is used herein to refer to reaction mixtures to which no Lewis base is added as a controlling agent. Minor amounts of Lewis base may be generated in situ during the reaction, but such amounts are inadequate to control the reaction. The reaction conditions required contemplate the presence of larger amounts of Lewis acid than that taught by the prior art. Typically the catalytic excess is at least 0.5 preferably at least 0.8 and most preferably at least 1 equivalent of Lewis acid per equivalent of acylating group. We have found that the excess of Lewis acid needed for optimum selectivity of acylation varies with the basicity of the aromatic compound. However, given this disclosure, the particular optimum for each aromatic compound is readily ascertainable by those skilled in the art.

The reaction conditions found to be necessary to prepare outstandingly high purity carbonyl compounds substantially free of ortho isomers are not taught or suggested by the prior art and in fact are contrary to the generally held beliefs of Friedel-Crafts chemistry. Conventionally, a moderate excess of Lewis acid usually up to about 0.4 equivalents per equivalent of carbonyl groups in the reagent system is used in Friedel-Crafts reactions. We have found that for many of the unsubstituted (in diacylation) or substituted aromatic compounds defined above a large excess of Lewis acid yields a more isomerically pure product. Prior art Friedel-Crafts reactions of this type were conducted using a Lewis acid to monomer ratio well below that needed for the production of products having the desired isomeric purity. Thus traditional Friedel-Crafts chemistry suggests the use only of a moderate excess of Lewis acid.

The compound produced contains catalyst residuents complexed to the carbonyl group. Decomplexation can be accomplished by treating the reaction mixture with a decomplexing base after completion of the reaction. The base can be added to the reaction medium or the reaction medium can be added to the base. The decomplexing base must be at least as basic towards the Lewis acid as the basic groups on the polymer chain. Such decomplexation preferably should be effected before isolation of the product from the reaction mixture.

The following examples illustrate the process of this invention using a variety of Lewis acids, Lewis bases, diluents and reagents. It is to be understood that other reactants and reaction media within the scope of the teaching of this invention can be employed, if desired.

EXAMPLE 1

To an agitated mixture of lithium chloride (3.18 g., 0.075 mole) and aluminium chloride (20 g., 0.15 mole) in dichloroethane (20 ml) at $-15°$ C. was added dropwise a mixture of 4-fluorobenzoyl chloride (8 g., 0.05 mole) and fluorobenzene (4.8 g., 0.05 mole) in dichloroethane (7 ml). The reaction mixture was removed from the water bath after one hour, stored at 0° C. for three hours then at room temperature overnight.

The reaction mixture was then slowly added to 100 mls of a stirred mixture of ice and dilute aqueous hydrochloric acid, the organic phase separated and the aqueous phase was washed with two 50 ml aliquots of ether. The combined organic phases were then washed with 50 ml of dilute sodium hydroxide solution, then water, separated and dried over anhydrous magnesium sulfate. The dried solution was filtered to remove the drying agent and the solvents removed in a rotary evaporator. 4,4'-Difluorobenzophenone (10.3 g., 94.5% yield) was obtained as a white solid of melting point 106.5°–109° C., whose purity was estimated by differential scanning calorimetry (DSC) by the reference test method described in United States Pharmacopaeia National Formulary, XIX, pages 980 to 983 (1975) and also by R.L. Blaine in the DuPont Company, Analytical Instruments Division Application Brief Number TA.80, and also by 1H and 19F nuclear magnetic resonance (NMR). The purity by the DSC method was estimated to be 97.2% and by the 1H NMR method about 95%.

EXAMPLE 2

In an experiment not using the process of the instant invention but following the teachings of traditional Friedel-Crafts chemistry, that is in the absence of lithium chloride and in the presence of aluminum chloride in an amount of 8 g., (0.06 mole), which is less than 1.5 equivalents per equivalent of 4-fluorobenzoyl chloride, the remaining ingredients being as described in example 1, the addition was commencd at 0° C. and the reaction mixture maintained at room temperature overnight. After work up as described in example 1, an orange oil was obtained in low yield. 1H NMR indicated only 50% of the product was the desired 4,4'-difluorobenzophenone, the remainder being isomers, impurities and starting materials. When this experiment was repeated using 20 g., (0.15 mole) of aluminium chloride the yield of crude reaction product increased to 93%, about half of which was the desired 4,4'-difluorobenzophenone.

EXAMPLE 3

Example 1 was repeated except that 20 g., (0.208 mole) fluorobenzene was used and the reaction mixture was kept at 0° C. overnight. The crude yield of 4,4'-difluorobenzophenone was 92.3% (m.p. 108°–110° C.; DSC purity 97.4 mol %, 1H NMR purity >95 mol %). 19F NMR indicated about 0.1% ortho acylation. After recrystallization from hexane the yield was 64%, the DSC purity was 99.75% and 19F NMR showed no evidence of ortho substituted (i.e., isomeric) impurities.

EXAMPLE 4

The procedure and materials of Example 3 were used except that 5.75 g., (0.025 mole) terephthaloyl chloride was used in place of 4fluorobenzoyl chloride and the reaction mixture was kept at about -5° C. for three days. The crude product 1,4-bis(4-fluorobenzoyl) benzene (6.98 g., 86.7% yield, m.p. 220.5°–222° C.) had a purity by 1H NMR greater than 95% and 19F NMR indicated no ortho isomers to be present.

EXAMPLE 5

The procedure and materials of Example 1 were used except that dimethylformamide (5.2 ml.,0.067 mol.) was used in place of lithium chloride, terephthaloyl chloride (5.75 g., 0.028 mol) in place of 4fluorobenzoyl chloride, and the reaction mixture was left for a further two days at room temperature). After work up the 1,4-bis(4-fluorobenzoyl)benzene obtained (6.91 g., 85.8% yield, m.p. 211.5217° C.) had a DSC purity of 95%.

EXAMPLE 6

The materials and procedure of Example 5 were used except that butyronitrile (6.5 ml, 0.075 mole) was used instead of dimethylformamide and the reaction mixture was kept at 0° C. overnight. The crude 1,4-bis(4-fluorobenzoyl)benzene obtained (9.91 g., 123% yield, m.p. 207.5°–212° C.) was 85% pure by 1H NMR (i.e. it contained nearly a quantitative yield of the desired product, the impurities being volatile at its melting point as the DSC purity was over 99%).

EXAMPLE 7

The materials and procedure of Example 5 were used except that the butyronitrile was omitted and the reaction mixture was kept at room temperature overnight. The crude 1,4-bis(4-fluorobenzoyl)benzene obtained (9.1 g., 83% yield) was 80% pure by 1H NMR.

EXAMPLE 8

To an agitated mixture of lithium chloride (3.18 g., 0.075 mole) and aluminium chloride (20 g., 0.15 mole) in dichloroethane (20 ml) at about −15° C. was added 4-fluorobenzoyl chloride (9.6 g., 0.06 mole) and diphenyl ether (4.25 g., 0.025 mole) in dichloroethane (10 ml). The reaction mixture was maintained at −15° to −17° C. for one hour then 0° C. for three hours then left at about −5° C. for three days. After working up as described in EXAMPLE 1 the 4,4'-bis(4-fluorobenzoyl)diphenyl ether obtained (9.34 g., 90% yield, m.p. 214.5°–215.5° C.) had a 1H NMR purity of over 99% and the DSC purity was 99.5%.

EXAMPLE 9

The materials and procedures of Example 8 were repeated except that the lithium chloride was omitted and the reaction was held at about −5° C. for three days, after one hour at −15° C. The 4,4'-bis(4fluorobenzoyl)diphenyl ether obtained (10.36 g., 100% yield, m.p. 213215° C.) had a 1H NMR purity of >95% and a DSC purity of 97.6%. 19F NMR indicated an absence of ortho-substituted isomers.

EXAMPLE 10

In an experiment not following the teachings of the instant invention Example 9 was repeated except that no lithium chloride was used, only 9.6 g., (0.072 mole) aluminium chloride was present and the reaction mixture was kept at 0° C. overnight then worked up. 3.92 g., (38% yield) of crude 4,4'-bis(fluorobenzoyl)diphenyl ether of 1H NMR purity 80% was obtained.

EXAMPLE 11

To an agitated mixture of aluminium chloride (20 g., 0.15 mole) and lithium chloride (3.18 g., 0.075 mole) and dichloroethane (20 ml) at −15° C. wash slowly added toluene (4.6 g., 0.05 mole) and acetyl chloride (3.93 g., 0.05 mole) in dichloroethane (10 ml). The reaction mixture was left at −15° C. for one hour then allowed to warm up to room temperature overnight. After working up as described in Example 1, the 4-methylacetophenone obtained (7.17 g.), had a 1H NMR estimated purity of about 95%. 1H NMR showed less than 2% ortho isomers.

EXAMPLE 12

The materials and procedures of Example 11 were followed except that benzoyl chloride (7.0 g., 0.05 mole) was used instead of acetyl chloride. The 4-methylbenzophenone obtained (8.62 g., 88% yield) had a 1H NMR purity of 95% and a DSC purity of 97.7%. Gas chromatography (G.C.) indicated the presence of less than 2% ortho isomers.

EXAMPLE 13

To an agitated mixture of lithium chloride (3.18 g., 0.075 mole) and aluminium chloride (20 g., 0.15 mol) in dichloroethane (20 ml) was slowly added diphenyl ether (8.51 g., 0.05 mole) and acetyl chloride (3.93 g., 0.05 mol) in dichloroethane (7 ml) following the procedure of example 12. The 4-phenoxyacetophenone obtained (9.57 g., 90.3% yield, m.p. 43.5°–51° C. had 1H NMR purity of 90%.

EXAMPLE 14

The materials and procedures of Example 13 were used except that acetic anhydride (5.1 g., 0.05 mole) was used instead of acetyl chloride. The 4-phenoxyacetophenone obtained (9.75 g., 92% yield, m.p. 46°–51.5° C.) had a 1H NMR purity of 90%, the major impurity being unreacted diphenyl ether.

EXAMPLE 15

The materials and procedures of Example 13 was used except that benzoyl chloride (7.03 g., 0.05 mole) was used instead of acetyl chloride. The p-phenoxybenzophenone obtained (12.83 g., 93.6% yield) had a 1H NMR purity of 90%, unreacted diphenyl ether being the main impurity.

EXAMPLE 16

The materials and procedures of Example 13 were used except that only 4.20 g., (0.025 mole) of diphenyl ether were used and 4chlorobenzoyl chloride (10.5 g., 0.06 mole) was used instead of acetyl chloride. The reaction product was poured into dilute hydrochloric acid-ice mixture, separated, suspended in methanol, filtered and dried in vacuum at 80° C. (This procedure was used because this product is insoluble in common solvents.) The 4,4'-bis(4-chlorobenzoyl)diphenyl ether obtained (10.84 g., 97% yield, m.p.244°-248° C.) had a DSC purity of 98.1%.

EXAMPLE 17

To an agitated mixture of lithium chloride (3.18 g., 0.075 mole) and aluminium chloride (20 g., 0.15 mole) in dichloroethane cooled to below −10° C. was added anisole (5.41 g., 0.05 mole) and benzoyl chloride (7.03 g., 0.05 mole) in dichloroethane (10 ml). The reaction mixture was held below −10° C. for one hour then allowed to come to room temperature overnight. The 4-methoxybenzophenone produced (9.55 g., 90.1% yield) had a gas chromatograph/mass spectrometer estimated purity of over 95% with 2% ortho isomers.

EXAMPLE 18

To a solution of diphenyl ether (3.57 g., 0.021 mole) in dichloroethane (15 ml) at −15° C. was added, by means of a bubbler, phosgene (0.87 g., 0.01 mole). The combined reactants were then added to an agitated mixture of lithium chloride (0.64 g., 0.015 mole) and aluminum trichloride (3.67 g., 0.0275 mole) in dichloroethane (20 ml) at −15° C. The reaction mixture was allowed to warm up to room temperature over 1.25 hours. After 68 hours at room temperature, the reaction mixture was worked up as described in example 1 to yield crude 4,4'-diphenoxy-benzophenone (2.2 g, 60% yield) of DSC purity 96.6%.

EXAMPLE 19

The procedure and materials of example 8 were used except that the same volumes of carbon disulfide are used as diluent instead of dichloroethane. The crude 4,4'-bis (4-fluorobenzoyl)diphenyl ether obtained (9.25 g., 89.4% yield) had a DSC purity of 95%. 1H and 19F NMR both indicated 95% purity.

EXAMPLE 20

To an agitated mixture of aluminum tribromide (30.0 g., 0.113 mole) in orthodichlorobenzene at −14° C. was slowly added over 5 minutes a mixture of 4-fluorobenzoyl chloride (4.0 g., 0.025 mole) and fluorobenzene (2.4 g., 0.025 mole). The mixture was then maintained at −12° C. for one hour and then allowed to warm up to room temperature overnight then worked up as described in example 1. The crude 4,4'-difluorobenzophenone obtained (3.5 g., 64% yield) had a 90% purity with 0.5% ortho impurities and 5 other small impurity peaks by 19F NMR. 1 HNMR indicated 95% purity with 5% unreacted acid chloride.

EXAMPLE 21

The materials and procedures of example 20 were followed except that only 15 g., (0.056 mole) aluminum tribromide was used. The crude 4,4'-difluorobenzophenone obtained (1.13 g., 20.7% yield) had a purity of 70% with 0.5% ortho impurities and 16 other small impurity peaks by 19F NMR. 1 HNMR indicated 70% purity with about 30% unreacted acid chloride.

EXAMPLE 22

The materials and procedures of example 20 were used except that diphenyl ether (2.13 g., 0.0125 mole) was used instead of fluorobenzene and 4.8 g., (0.03 mole) fluorobenzoyl chloride was used. The crude 4,4'-bis (4-fluorobenzoyl)diphenyl ether obtained (5.9 g., about 100% yield) had a purity of 60% by 19F NMR with three impurity peaks. 1 H NMR indicated a 70% purity the remainder being starting materials.

EXAMPLE 23

The materials and procedures of example 22 were used except that 15.0 g., (0.056 mole) aluminum bromide was used. The crude 4,4'bis(4-fluorobenzoyl) diphenyl ether obtained (5.4 g., 100% yield, m.p. 209°-212.5° C.) had a DSC purity of 95.6%. 1H NMR indicated a 95% purity with 5% starting materials. 19F NMR indicated purity was 90-95%.

EXAMPLE 24

The materials and procedures of example 12 were used except that the lithium chloride was omitted. The crude 4-methylbenzophenone obtained (8.15 g., 83.2% yield) had a purity as estimated by G.C. and 1H NMR of 90%.

EXAMPLE 25

Example 17 was repeated except that the lithium chloride was omitted. The crude 4-methoxybenzophenone obtained (7.5 g., 70.5% yield) was found to contain no ortho isomers as measured by G.C.

EXAMPLE 26

In an experiment not following the teachings of the instant invention, Example 11 was repeated except that no lithium chloride was used and only 8.0 g (0.06 mole) aluminum chloride was present. After working up in the same way as example 11, 4-methylacetophenone was obtained with a 1H NMR purity of 80 to 85%. GC/MS indicated an impurity with a mass of 324 Daltons was present.

EXAMPLE 27

In an experiment not following the teachings of the instant invention, Example 14 was repeated except that no lithium chloride was used and only 8.0 g (0.06 mole) aluminum chloride was present. The 4phenoxyacetophenone obtained had an 1H NMR purity of 80 to 85%, the main impurities being about 5% unreacted diphenyl ether and about 10% of the diacetylated product.

EXAMPLE 28

In an experiment not following the teachings of the instant invention, Example 16 was repeated except that no lithium chloride was used and only 9.6 g (0.072 mole) aluminum chloride was present. The 4,4'-bis(4-chlorobenzoyl)diphenyl ether was obtained in 86% yield.

What is claimed is:

1. A process for the preparation of an aromatic carbonyl compound having the formula (R)$_s$ArDCOBD(R')$_t$, (R)$_s$ArDCOBDCOArD(R)$_s$,
(R)$_s$ArDCODAr(R)$_s$, or
(R')$_t$DBCOArDCOBD(R')$_t$ wherein each s and t is independently 1, 2 or 3 and each R, Ar, B, D, Y and R, is independently as defined below, which comprises reacting a first reactant, consisting of a substituted or unsubstituted aromatic compound containing at least one activated hydrogen of the formula (R)$_s$ArDH wherein Ar is a homo or heteroaromatic mono-, di-, or tricyclic moiety or a fused homoaromatic ring system containing less than 20 aromatic carbon atoms or a heteroaromatic system containing less than 8 nitrogen atoms, each R is as defiend below and D is —(ZAr)$_n$—(ZAr)$_m$—(ZAr)$_p$— wherein n, m, and p are each independently 0, 1, 2 or 3, provided that n+m+p is less than 4, and Z is —CO—, —SO$_2$—, —(CO)—C$_6$H$_4$—(CO)—or —O—(CF$_2$)$_q$O— or V, provided that when n+m+p>0, any Ar group comprising an activated hydrogen atom is also linked to a V group, where V is a divalent radical of the formula —O—, —S—, —N=N—, —(CF$_2$)$_q$—,
—(CH$_2$)$_q$—or —C(CH$_3$)$_2$— wherein q is 1 to 20;
with a second reactant, consisting of phosgene, or a monofunctional acyl compound of the general formula YCOBD(R')$_t$ or O(COBD(R')$_t$)$_2$ or a difunctional compound of the general formula

YCOBDCOY wherein each B is independently a divalent substituted or unsubstituted aliphatic or cycloaliphatic group or Ar, and R and R' which may be the same or different are a H, Br, Cl or F atom or a hydroxy, alkoxy, alkyl, aralkyl, unsubstituted or mono- or disubstituted amiono, nitro, ester, acid, amide, or imide group, and each Y represents a Br, Cl or F atom or a hydroxy or alkoxy group, subject to the proviso that any aromatic ring which contains an activated hydrogen also contains less than 2 alkoxy groups and to the further proviso that the aromatic carbonyl compound contains less than 2 identical directly linked sequences containing at least one —SO$_2$—or —CO—;
in a reaction medium comprising:
  (A) a covalent organic Lewis base in an amount from 0.1 to 4 equivalents per equivalent of acid, ester, or acid halide group in the reactants;
  (B) a Lewis acid selected from the group consisting of aluminum trichloride, aluminum tribromide, antimony pentachloride, antimony pentafluoride, indium trichloride, gallium trichloride, boron trichloride, boron trifluoride ferric chloride, stannic chloride, titanium tetrachloride, and molybdenum pentachloride, in an amount of about one equivalenet per equivalent of carbonyl, or other basic species in the reactants plus one equivalent per equilent of Lewis base plus an amount effective to act as a catalyst for the reaction; and
  (C) a non-protic diluent in an amount from about 20 to about 93% by weight, based on the weight of the total reaction mixture;

2. A process according to claim 1 wherein the aromatic carbonyl compound produced has the structure (R')$_t$DBCOArDCOBD(R')$_t$ and the first reactant contains 2 activated hydrogen atoms.

3. A process according to claim 1 wherein the aromatic compound is selected from benzene, toluene, ethyl benzene, fluorobenzene, chlorobenzene, bromobenzene, anisole, ethoxy benzene, 3-chloroanisole, naphthalene, anthracene, and

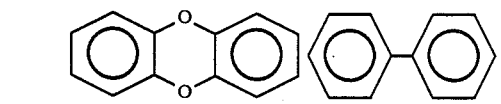

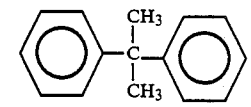

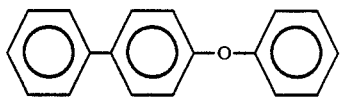

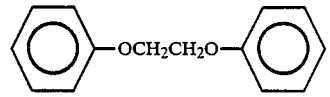

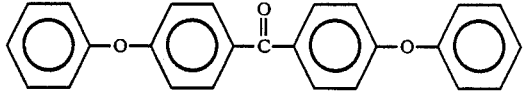

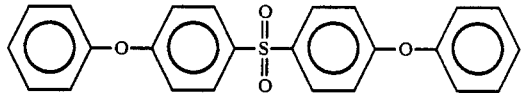

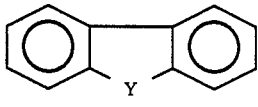

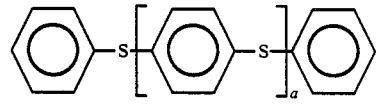

-continued

or

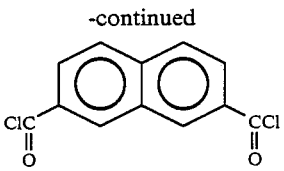

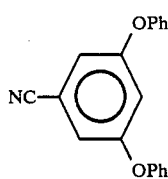

wherein each a is independently 0, 1 or 2.

4. A process according to claim 1 wherein the organic mono- or di-acid compound is selected from acetic anhydride, acetyl chloride, oxalyl dichloride, adipolyl dichloride, benzoyl chloride, 4-fluorobenzoyl chloride 4-chlorobenzoyl chloride, 3-nitrobenzoyl chloride, terephthaloyl chloride, isophtahaloyl chloride, phthaloyl chloride, phthalic anhydride, naphthoyl chloride, tetrabromophthalloyl chloride, and compounds of the following formulas

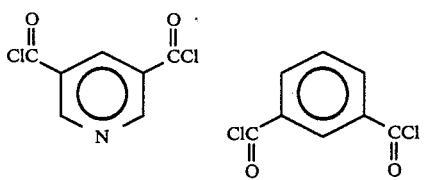

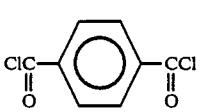

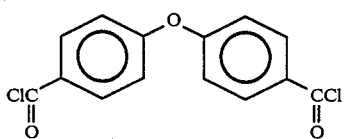

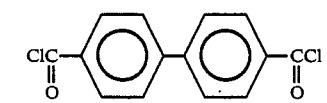

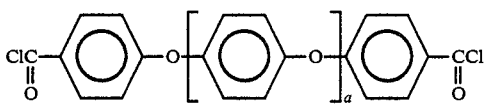

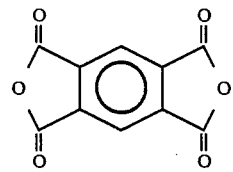

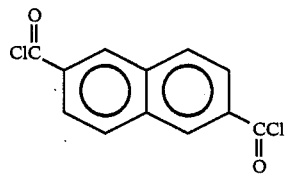

-continued

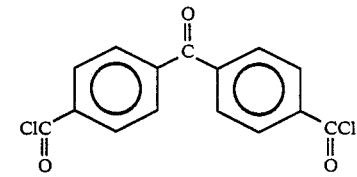

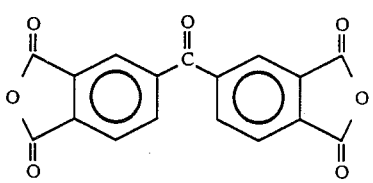

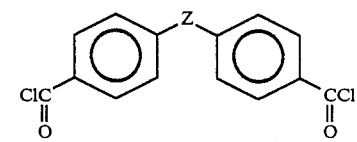

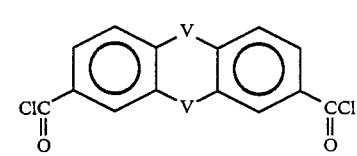

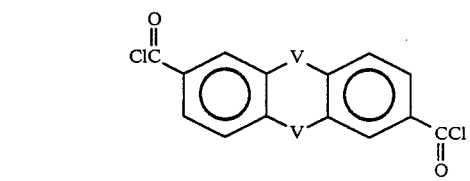

where a is 0, 1 or 2.

5. A process according to claim 1 wherein the Lewis base is selected from orgainc amides, amins, esters, ethers, ketones, nitriles, nitro compounds, phosphines, phosphine oxides, phosphoramides, sulfides, sulfones, sulfonamides, and sulfoxides.

6. A process according to claim 1 wherein the diluent is selected from methylene chloride, carbon disulfide, o-dichlorobenzene, 1,2,4-trichlorobenzene, o- difluorobenzene, 1,2-dichloroethane, tetrachloroethane, 1,1,2,2-tetrachloroethane and mixtures thereof.

7. A process according to claim 1 wherein the Lewis base is a covalent orgainc compound selected from the group consisting of acetone, benzophenone, methyl acetate, ethylene carbonate, N-methylformamide, acetamide, N,N-dimethylformacetamide, N-methylpyrrolidone, urea, tetramethylurea, N-acetylmorpholine, dimethyl sulfoxide, N,N-dimehtylformamide, diphenyl sulfone, dimethyl sulfone, N,N-dimethylmethanesulfonamide, phosphoryl chloride, phenylphosphonyl chloride, pyridine-N-oxide, triphenylphosphine oxide, trioctylphosphine oxide, nitropropane, nitrobenzene, benzonitrile, n-butyronitrile, methyl ether, tetrahydrofuran, dimethyl sulfide, trimethylamine, N,N,N',N -tetramethylethylenediamine, N,N-dimethyldodecyl amine, imidazole, pyridine, quinoline, isoquinoline, benzimidazole, 2,2,bipyridine, o-phenanathroline, and 4-dimethylaminopyridine.

* * * * *